(12) United States Patent
Margheritini

(10) Patent No.: US 11,377,414 B2
(45) Date of Patent: *Jul. 5, 2022

(54) PLANT AND PROCESS FOR CONCENTRATING TARTARIC ACID

(71) Applicant: DISTILLERIE MAZZARI S.P.A, Sant'agata Sul Santerno (IT)

(72) Inventor: Emidio Margheritini, Sant'agata Sul Santerno (IT)

(73) Assignee: DISTILLERIE MAZZARI S.P.A, Sant'agata Sul Santerno (IT)

( * ) Notice: Subject to any disclaimer, the term of this patent is extended or adjusted under 35 U.S.C. 154(b) by 0 days.

This patent is subject to a terminal disclaimer.

(21) Appl. No.: 17/005,992

(22) Filed: Aug. 28, 2020

(65) Prior Publication Data

US 2021/0061747 A1 Mar. 4, 2021

(30) Foreign Application Priority Data

Aug. 30, 2019 (IT) .................. 102019000015288

(51) Int. Cl.
*B01D 1/26* (2006.01)
*C07C 51/44* (2006.01)
(Continued)

(52) U.S. Cl.
CPC ............ *C07C 51/44* (2013.01); *B01D 1/0082* (2013.01); *B01D 1/14* (2013.01); *B01D 1/26* (2013.01);
(Continued)

(58) Field of Classification Search
CPC ....... C07C 51/43; C07C 51/44; C07C 51/445; C07C 55/02–21; B01D 1/0082;
(Continued)

(56) References Cited

U.S. PATENT DOCUMENTS 1,513,305 A 10/1924 Augustin
1,831,121 A * 11/1931 Kermer .................... B01D 1/12
159/45

(Continued)

FOREIGN PATENT DOCUMENTS

WO 2012156646 A1 11/2012
WO 2018019534 A1 2/2018

OTHER PUBLICATIONS

Italian Search Report for IT Patent Application No. 201900015288, dated Mar. 10, 2020, 9 pages.

*Primary Examiner* — Jonathan Luke Pilcher
(74) *Attorney, Agent, or Firm* — Armstrong Teasdale LLP

(57) ABSTRACT

A plant for concentrating a tartaric acid solution includes a first and a second evaporation unit arranged in series, a pump for feeding a diluted tartaric acid solution into the first evaporation unit, a barometric condenser placed downstream of the second evaporation unit, and a system for feeding a first low-temperature vapor into the first evaporation unit. A process for concentrating tartaric acid includes providing a plant according to the above description, performing a first concentration, by evaporation, of the diluted tartaric acid solution, inside the first evaporation unit, and performing a second concentration, by evaporation, of the partially concentrated tartaric acid solution from the first evaporation unit, inside the second evaporation unit. The plant and process have the advantages of ensuring low energy consumption, allowing concentration of solutions tending to crystallization, and allowing the continuous measurement of the tartaric acid concentration to be concentrated.

4 Claims, 2 Drawing Sheets

(51) Int. Cl.
   *B01D 1/00*   (2006.01)
   *B01D 5/00*   (2006.01)
   *B01D 3/38*   (2006.01)
   *B01D 1/14*   (2006.01)

(52) U.S. Cl.
   CPC ............... *B01D 3/38* (2013.01); *B01D 5/006* (2013.01); *B01D 5/0048* (2013.01); *C07C 51/445* (2013.01)

(58) Field of Classification Search
   CPC .......... B01D 1/0094; B01D 1/06; B01D 1/12; B01D 1/14; B01D 1/26; B01D 3/065; B01D 3/146; B01D 3/34; B01D 3/346; B01D 3/38; B01D 5/0048; B01D 5/006; B01D 5/0081; C12F 3/06
   USPC .......... 159/16.1, 16.3, 17.1, 17.2, 27.2, 27.3
   See application file for complete search history.

(56) References Cited

U.S. PATENT DOCUMENTS

| | | | |
|---|---|---|---|
| 2,184,579 A * | 12/1939 | Brucke | B01D 3/38 |
| | | | 203/79 |
| 2,510,233 A * | 6/1950 | Kermer | B01D 1/26 |
| | | | 159/3 |
| 2,524,753 A | 10/1950 | Betts | |
| 2,838,108 A * | 6/1958 | Sumiya | B01D 1/26 |
| | | | 159/17.1 |
| 3,289,736 A | 12/1966 | Rosenblad | |
| 3,855,079 A | 12/1974 | Greenfield et al. | |
| 4,279,693 A | 7/1981 | Kuehnlein et al. | |
| 2019/0161365 A1 | 5/2019 | Buttner et al. | |
| 2021/0061747 A1 * | 3/2021 | Margheritini | B01D 3/065 |

\* cited by examiner

PLANT AND PROCESS FOR CONCENTRATING TARTARIC ACID

CROSS-REFERENCE TO RELATED APPLICATIONS

This application claims the benefit of priority to Italian Patent Application No. 102019000015288, having a filing date of Aug. 30, 2019, which is hereby incorporated by reference in its entirety.

FIELD OF THE INVENTION

The present invention relates to a plant and process for concentrating tartaric acid, in particular by means of a continuous process.

BACKGROUND ART

Tartaric acid is a white, crystalline diprotic organic acid. It is naturally present in many plants, especially grapes and tamarind (as well as other fruits). One of the salts thereof, potassium bitartrate, commonly known as cream of tartar, develops naturally in the winemaking process.

Industrially, tartaric acid is produced in large amounts. It is obtained from lees, a by-product of wine fermentation.

Tartaric acid has various fields of application. One of the uses thereof, when mixed with sodium bicarbonate, is as a leavening agent. As such, it can be added to foods as an antioxidant agent or to impart a sour taste. It is often added to certain foods such as candies, jams, and fruit juices to impart a sour taste thereto. It is used as an antioxidant and emulsifier in bread-making and in the preparation of leavening agents for cakes and bread. It is used in wine to balance the acidity thereof. It is used in the preparation of medicines: for example, mixed with sodium bicarbonate, it is used in the preparation of effervescent products to aid digestion. As for industrial applications, tartaric acid has the ability to chelate metal ions such as calcium and magnesium. Therefore, it is used both in the agricultural industry and in the metallurgical industry, to favor, for example, the complexation of micronutrients present in soil or for cleaning metal surfaces (aluminum, copper, iron, or metal alloys).

To date, the production process of tartaric acid includes a concentration step in which the diluted tartaric acid undergoes a concentration process, in order to obtain concentrated tartaric acid.

This process usually takes place inside an evaporation plant. The physical principle on which this type of plant is based is an evaporation principle which exploits the different boiling points (and therefore evaporation) of the components of a solution (diluted tartaric acid in this case). Indeed, the solutions subjected to this type of process usually consist of a solute having a higher boiling point than that of the solvent. Thereby, by heating the solution up to the solvent boiling temperature, the latter will evaporate, concentrating the solution.

The possibility of arranging a plant capable of concentrating tartaric acid which is produced efficiently and with low energy consumption is thus a need felt in the market.

Furthermore, the tartaric acid solutions to be concentrated are usually solutions whose tendency to crystallization is high, which makes them problematic solutions when placed in an evaporation plant. Indeed, using an easy crystallization solution inside an evaporation plant can cause the formation of encrustations inside the walls of the plant where the solution flows, with consequent damage to the plant itself.

When working with an evaporation plant for concentrating solutions, another parameter to consider is the measurement of the concentration of the solution to be concentrated. In fact, it is important that the solution is only extracted from the plant when it is certain that the solution has reached a certain concentration value. Therefore, the identification and use, within the plant, of a system which allows the continuous measurement of the concentration of the solution to be concentrated is an important aspect for the good yield of the concentration process.

SUMMARY OF THE INVENTION

Therefore, it is object of the present invention to provide a plant and process for concentrating tartaric acid which is efficient, ensures low energy consumption, allows an easy concentration of solutions tending to crystallization, and has a system for the continuous measurement of the tartaric acid concentration to be concentrated.

This object is achieved by a plant and process for concentrating tartaric acid as outlined in the appended claims, the definitions of which form an integral part of the present patent application.

BRIEF DESCRIPTION OF THE DRAWINGS

The invention will be better understood from the following detailed description of preferred embodiments thereof, given by way of not limiting example, with reference to the accompanying drawings, in which.

In the accompanying drawings, equal or similar elements will be indicated by the same reference numerals.

DETAILED DESCRIPTION OF THE INVENTION

Figure 1:
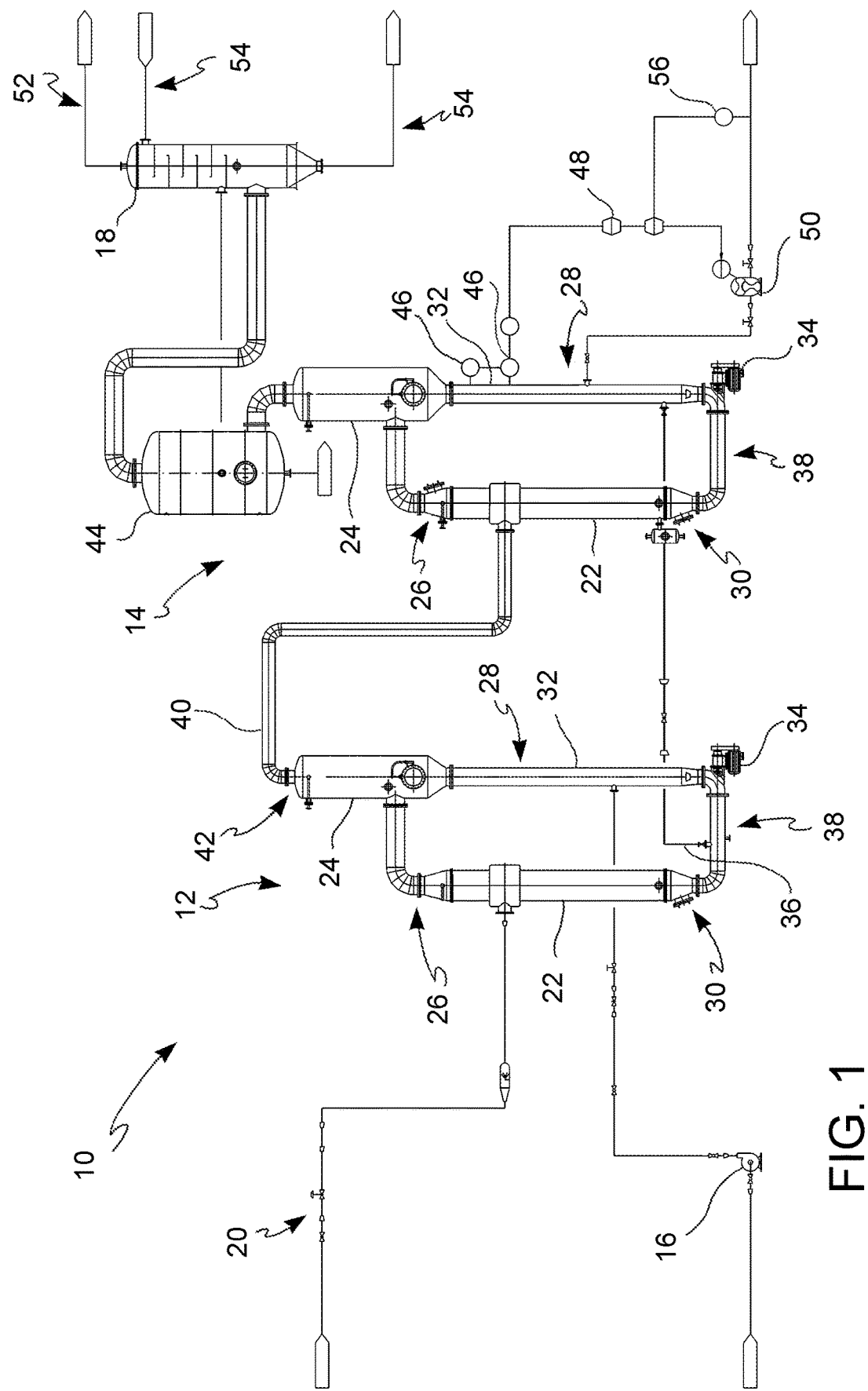
FIG. 1 shows the plant for concentrating tartaric acid according to the present invention.
Figure 2:
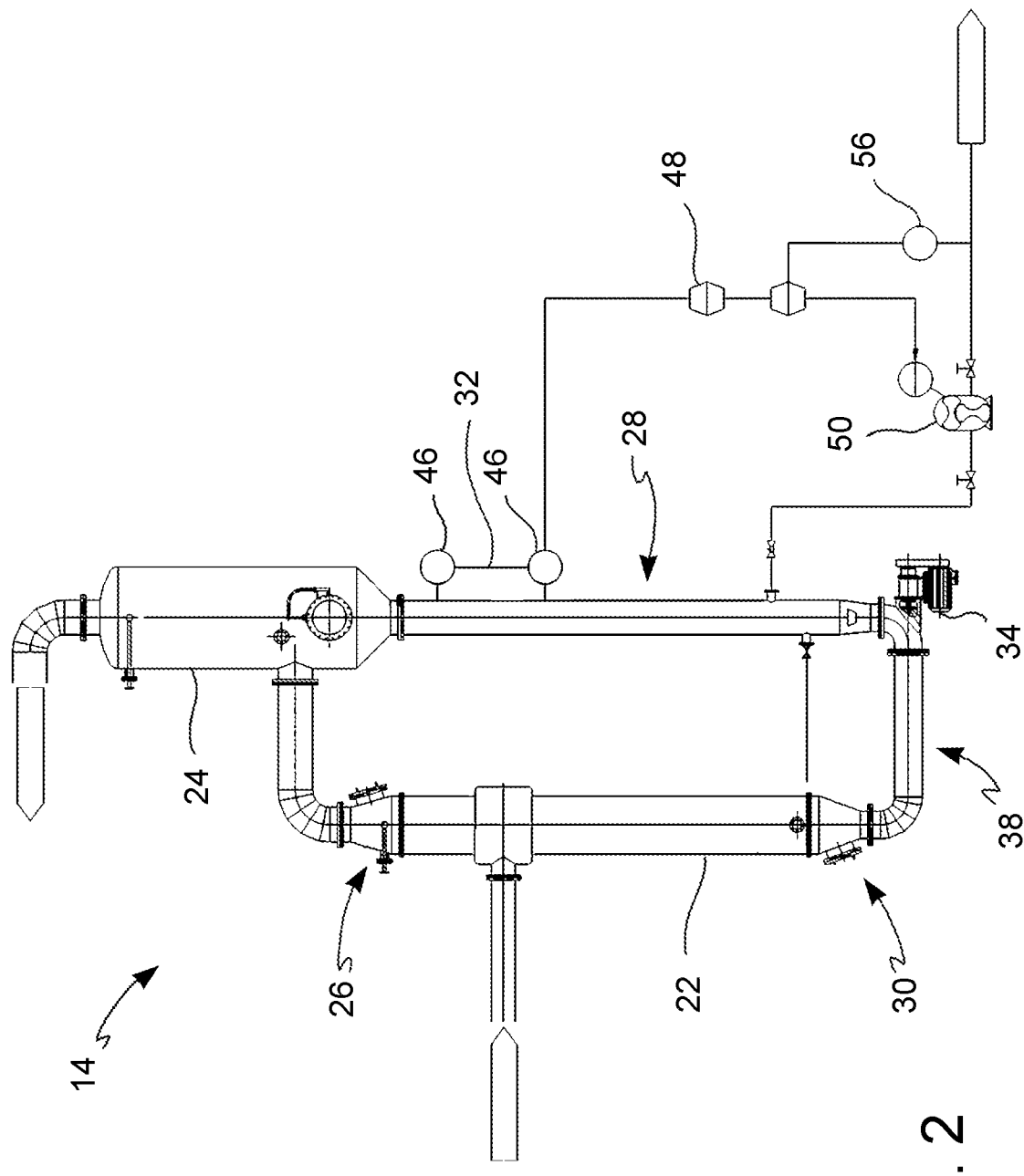
FIG. 2 shows a detail of the plant of FIG. 1.

With reference to FIGS. 1 and 2, a first object of the present invention is shown, i.e., a plant 10 for concentrating a tartaric acid solution comprising:

a first 12 and a second 14 evaporation unit, in which said first 12 and second 14 evaporation units are arranged in series;

a pump for feeding a diluted tartaric acid solution 16 into said first evaporation unit 12;

a barometric condenser 18 placed downstream of said second evaporation unit 14, a system for feeding a first low-temperature vapor 20 into said first evaporation unit 12.

Preferably, the tartaric acid solution comprises tartaric acid and sulfuric acid, the latter at a concentration between 3% and 5%, preferably about 4%.

Preferably, each of said first 12 and second 14 evaporation units comprises:

i) a heat-exchange evaporation chamber 22, in which the first vapor comes into contact with the tartaric acid solution to be concentrated, ii) a liquid-aeriform separation chamber 24, connected to a head portion 26 of said evaporation chamber 22.

Preferably, the first vapor is saturated aqueous vapor having a temperature between 70° C. and 90° C., preferably about 80° C.

Preferably, said heat exchange evaporation chamber 22 is an apparatus known to those skilled in the art in which thermal energy is exchanged between two elements having different temperatures. According to a preferred embodiment of the present invention, the above elements are the tartaric acid solution and the first vapor. In fact, the heat-exchange evaporation chamber 22 receives the first low-temperature vapor, by means of which the exchange of thermal energy takes place between the first vapor and the tartaric acid solution. This thermal energy exchange allows to heat the solution until the boiling temperature of the tartaric acid solution is reached, resulting in the formation of a second vapor (vapor of the solvent contained in the tartaric acid solution) and accumulation in the head portion 26 of the evaporation chamber 22 of an aeriform phase consisting of the aforesaid second vapor. Indeed, the amount of energy required for evaporation is supplied by the first low-temperature vapor.

Preferably the heat-exchange evaporation chamber 22 of the first evaporation unit 12 receives the first low-temperature vapor from the system for feeding the first low-temperature vapor 20.

The liquid-aeriform separation chamber 24 is also preferably an apparatus known to those skilled in the art in which a separation of the aeriform phase coming from the head portion 26 of the evaporation chamber 22 is carried out. In fact, the aforesaid aeriform phase may also comprise, in addition to the second vapor produced by the evaporation of the tartaric acid solution, the tartaric acid particles dragged from the evaporation chamber 22. Therefore, inside the liquid-aeriform separation chamber 24, there is a separation between the properly aeriform phase (second vapor) and the dragged tartaric acid particles.

Two unitary operations are thus carried out inside the evaporation chamber 22 and the separation chamber 24: the heat exchange between the first vapor and the tartaric acid solution and the separation between the properly aeriform phase and the dragged tartaric acid particles.

Preferably inside the heat-exchange evaporation chamber 22 of the second evaporation unit 14, the tartaric acid solution has a temperature between 50° C. and 60° C., preferably about 56° C., and a pressure between 0.07 BarA and 0.11 BarA, preferably about 0.09 BarA. While on the other hand, preferably, inside the heat-exchange evaporation chamber 22 of the first evaporation unit 12, the tartaric acid solution has a temperature between 60° C. and 70° C., preferably about 66° C.

According to a preferred embodiment of the invention, the barometric condenser 18 is connected to a vacuum pump 52 and to a system for circulating water 54 inside the condenser. Advantageously, the barometric condenser 18 condenses the properly aeriform phase exiting the second evaporation unit 14.

Furthermore, preferably, the separation chamber 24 of the second evaporation unit 14 is connected to the barometric condenser 18 through an acidic solution separation chamber 44 being placed in an intermediate position between the separation chamber 24 of the second evaporation unit 14 and the barometric condenser 18. The function of the acidic solution separation chamber 44 is to separate any acidic residues present in the properly aeriform phase exiting the separation chamber 24 of the second evaporation unit 14.

Each of said first 12 and second 14 evaporation units also preferably comprises a connecting portion 28 which connects the liquid-aeriform separation chamber 24 to a bottom portion 30 of said evaporation chamber 22, in which said connecting portion 28 comprises a column 32 which extends along a vertical axis.

Preferably, the column 32 of the first evaporation unit 12 is connected to the pump for feeding a diluted tartaric acid solution 16, thus allowing the introduction of the diluted tartaric acid solution to be concentrated into the first evaporation unit 12 and therefore into the plant 10.

Each of said first 12 and second 14 evaporation units further comprises, preferably, a recirculation pump 34 for the tartaric acid solution operatively connected to said connecting portion 28, for recirculating the tartaric acid solution from said separation chamber 24 to said evaporation chamber 22.

According to a preferred embodiment, the tartaric acid particles, dragged from the evaporation chamber 22 and separated from the properly aeriform phase inside the liquid-aeriform separation chamber 24, fall by gravity into the column 32, joining the tartaric acid solution already present in the connecting portion 28.

The presence of the recirculation pump 34, allowing the recirculation of the tartaric acid solution, advantageously allows to have a forced-circulation plant 10 for concentrating a tartaric acid solution. The forced circulation creates a turbulent motion inside the tartaric acid solution which ensures a high exchange coefficient between the first vapor and the tartaric acid solution and allows an easy concentration of a solution tending to crystallization such as that used in the plant 10 according to the present invention.

Furthermore, the presence of recirculation pumps 34 and of a pair of evaporation units placed in series advantageously ensures low energy consumption.

According to a preferred embodiment of the plant 10 of the present invention, said first 12 and second 14 evaporation units are, preferably, connected by a pipe for transferring the partially concentrated tartaric acid solution 36 placed at a bottom portion 38 of said evaporation units 12; 14 and by a pipe for transferring the properly aeriform phase 40 from a head portion 42 of the separation chamber 24 of the first evaporation unit 12 to the evaporation chamber 22 of the second evaporation unit 14.

These connections not only allow the series connection of the two evaporation units 12; 14, but also the passage of the partially-concentrated tartaric acid solution and of the properly aeriform phase, created in the first evaporation unit 12, from the first evaporation unit 12 to the second evaporation unit 14. In particular, the pipe for transferring the partially concentrated solution 36 preferably connects a bottom portion of the connecting portion 28 of the first evaporation unit 12, placed downstream of the column 32, with a bottom portion of the column 32 of the second evaporation unit 14.

Still according to a preferred embodiment of the plant 10 according to the present invention, the column 32 of the connecting portion 28 of the second evaporation unit 14 preferably and advantageously comprises a pair of facing-flange pressure sensors 46, each coupled to a fluid separator preferably in tantalum, in which the pressure sensors 46 are placed at a distance between 1.5 m and 2.5 m, preferably about 2 m, and are connected to a differential pressure transmitter 48 in turn connected to a volumetric pump 50 for extracting concentrated tartaric acid from the plant 10, said volumetric pump 50 being controlled on the basis of an electrical signal sent by the differential pressure transmitter 48 between 4 mA and 20 mA.

Preferably, said control takes place by means of a feedback control adapted to allow the extraction of concentrated tartaric acid from the plant 10 only when the pressure value detected by the differential pressure transmitter 48 is within ideal values between 1 kg/l and 1.5 kg/l, values which correspond to the sending, by the differential pressure transmitter 48, of the electrical signal between 4 mA and 20 mA.

The pair of sensors 46 is preferably placed at the aforesaid distance along a vertical axis along which the column 32 of the connecting portion 28 extends.

As known, the fluid separators are used when the pressure sensors 46 to which they are coupled must not come into contact with the process fluid. Therefore, they serve the function of transmitting the pressure variations of the fluid flowing in the plant 10 to the instrument (the differential pressure transmitter 48, in the case of the present invention), while keeping it isolated from the pressure sensor 46. Suitable types of fluid separators according to the present invention are, for example, fluid separators in titanium, nickel, tantalum. The fluid separators of the present invention are preferably in tantalum.

The differential pressure transmitter 48 is also preferably connected to a flow rate sensor 56 placed downstream of the volumetric pump 50. The function of the flow rate sensor 56 is to measure the flow rate of concentrated tartaric acid exiting the plant 10. Preferably, the flow rate sensor 56 carries out a second control on the volumetric pump 50. Preferably said second control also takes place by means of a feedback control adapted to keep the flow rate within ideal values. Preferably said ideal values are between 0 m$^3$/h and 10 m$^3$/h.

For a detailed description of the operation and diagram of the signals transmitted by the pressure sensors 46, and by the flow rate sensors, to the volumetric pump 50, reference should be made to the following of the present description.

The present invention further relates to a process for concentrating tartaric acid comprising the steps of:

providing a plant 10 according to the above description;

performing a first concentration, by evaporation, of the diluted tartaric acid solution, inside the first evaporation unit 12;

performing a second concentration, by evaporation, of the partially concentrated tartaric acid solution from the first evaporation unit 12, inside the second evaporation unit 14;

According to a preferred embodiment of the present invention, the process for concentrating tartaric acid preferably comprises the following steps:

providing a plant 10 according to the above description;

performing a first concentration, by evaporation, of the diluted tartaric acid solution, inside the first evaporation unit 12;

performing a second concentration, by evaporation, of the partially concentrated tartaric acid solution from the first evaporation unit 12, inside the second evaporation unit 14;

setting, as a basal pressure difference ΔP measured between the first and second sensors of the pair of sensors 46 present in the column 32 of the connecting portion 28 of the second evaporation unit 14, the pressure difference which would be measured in a 2 m high water column, corresponding to a density of 1 kg/l, and assigning the zero value to said ΔP.

measuring the pressure of the tartaric acid solution flowing inside the column 32 of the connecting portion 28 of the second evaporation unit 14 by means of the aforesaid pair of pressure sensors 46;

sending the measured pressure values to the differential pressure transmitter 48, which, when detecting a ΔP value equal to a density between 1 kg/l and 1.5 kg/l, preferably about 1.3 kg/l, sends an electrical feedback control signal between 4 mA and 20 mA, preferably about 17 mA, to the volumetric pump 50 which controls the extraction of the concentrated tartaric acid solution from the second evaporation unit 14.

Therefore, the process for concentrating tartaric acid according to the present invention preferably begins with the introduction, by means of the feed pump 16, of the diluted tartaric acid solution into the column 32 of the connecting portion 28 of the first evaporation unit 12. From here the diluted tartaric acid solution flows, due to the recirculation pump 34, into the heat-exchange evaporation chamber 22 of the first evaporation unit 12. Here the diluted tartaric acid solution encounters the first low-temperature vapor, coming from the feed system 20, and an exchange of thermal energy takes place between the first vapor and the diluted tartaric acid solution. This exchange of thermal energy leads to an increase in the temperature of the diluted tartaric acid solution until the boiling temperature thereof is reached. Once the aforesaid boiling temperature has been reached, the solvent contained within the solution begins to evaporate, creating a second vapor. An aeriform phase thus accumulates in the head portion 26 of the evaporation chamber 22, consisting of the aforesaid second vapor and any residual tartaric acid particles which are dragged during the evaporation. This aeriform phase then passes inside the liquid-aeriform separation chamber 24 of the first evaporation unit 12, in which the separation takes place between the properly aeriform phase (second vapor) and the tartaric acid particles dragged by the head portion 26 of the evaporation chamber 22. The tartaric acid particles dragged by the head portion 26 of the evaporation chamber 22 fall by gravity into the column 32 of the connecting portion 28 of the first evaporation unit 12, thus adding themselves to the diluted tartaric acid solution coming from the feed pump 16. The properly aeriform phase passes instead inside the pipe for transferring the properly aeriform phase 40 to enter the heat-exchange evaporation chamber 22 of the second evaporation unit 14 where it meets the partially concentrated tartaric acid solution coming from the first evaporation unit 12. In fact, the pipe for transferring the partially concentrated tartaric acid solution 36 which connects to a bottom portion of the column 32 extends from a bottom portion of the connecting portion 28, placed downstream of the column 32, of the first evaporation unit 12 of the connecting portion 28 of the second evaporation unit 14. Through this pipe 36 the partially concentrated tartaric acid solution passes from the first evaporation unit 12 to the second evaporation unit 14 and enters the column 32 of the connecting portion 28 of the second evaporation unit 14. The partially concentrated tartaric acid solution is transported here, due to the action of the recirculation pump 34, inside the heat-exchange evaporation chamber 22 of the second evaporation unit 14 where it meets the aforesaid properly aeriform phase and where a heat exchange between the two takes place. The properly aeriform phase heats the partially concentrated tartaric acid solution until it reaches the boiling temperature thereof. Once this temperature has been reached, the solvent of the partially concentrated solution begins to evaporate, creating, as for the first evaporation unit 12, an aeriform phase comprising a second vapor and any tartaric acid particles. As in the first evaporation unit 12, also in the second evaporation unit 14 the aeriform phase passes into the separation chamber 24 (of the second evaporation unit 14) where the separation between the properly aeriform phase (second vapor) and the tartaric acid particles takes place, which fall by gravity into the column 32 of the connecting portion 28 of the second evaporation unit 14. The properly aeriform phase of the second evaporation unit 14 instead passes inside the acidic solution separation chamber 44 where the separation of any acidic gases present in the properly aeriform phase takes place. The properly aeriform phase exiting the acidic solution separation chamber 44 passes inside the barometric condenser 18 where the condensable vapors are condensed and extracted from the plant 10, while any non-condensable gases are extracted by means of a vacuum pump 52.

The pair of pressure sensors 46 is present inside the column 32 of the connecting portion 28 of the second evaporation unit 14, the pair measuring the pressure of the tartaric acid solution in transit. The pressure measurement value is sent to the differential pressure transmitter 48 which when it detects a pressure value between 1 kg/l and 1.5 kg/l (preferably when it detects a pressure signal of about 1.3 kg/l), pressure values set as ideal set points, sends a signal (between 4 mA and 20 mA, preferably about 17 mA) to the volumetric pump 50, thus controlling the extraction of the concentrated tartaric acid solution from the second evaporation unit 14.

Downstream of the volumetric pump 50 there is also preferably a flow rate sensor 56, the purpose of which is to measure the flow rate of the concentrated tartaric acid solution exiting the second evaporation unit 14. If the measured range is between 0 m$^3$/h and 10 m$^3$/h, (preferably about 4.5 m$^3$/h), flow rates set as ideal set points, the flow rate sensor 56 sends a second feedback control signal to the volumetric pump 50, controlling the extraction activity of concentrated tartaric acid from the plant 10.

Therefore, the plant 10 and the process for concentrating tartaric acid according to the present invention have the advantages of ensuring low energy consumption, allowing an easy concentration of solutions tending to crystallization, and allowing the continuous measurement of the tartaric acid concentration to be concentrated.

The plant 10 and the process for concentrating tartaric acid according to the present invention also have the advantage of accurately obtaining concentrated tartaric acid, due to the repeatability provided by the double feedback control mechanism provided in the plant 10 and in the related process. The presence of the two feedback controls allows to maintain the pressure values, and therefore the concentration, of the concentrated tartaric acid and the values of the flow rate of concentrated tartaric acid leaving the plant 10 around ideal pre-set values, thus ensuring accuracy and repeatability.

What is claimed:

1. A plant for concentrating a tartaric acid solution, the plant comprising:
    a first evaporation unit and a second evaporation unit, wherein said first and second evaporation units are arranged in series;
    a pump for feeding a diluted tartaric acid solution into said first evaporation unit;
    a barometric condenser placed downstream of said second evaporation unit; and
    a system for feeding a first low-temperature vapor into said first evaporation unit, wherein the first low-temperature vapor has a temperature comprised between 70° C. and 90° C.,
    wherein each of said first and second evaporation units comprises:
        i) a heat-exchange evaporation chamber, in which vapor comes into contact with a tartaric acid solution to be concentrated,
        ii) a liquid-aeriform separation chamber, connected to a head portion of said heat-exchange evaporation chamber,
        iii) a connecting portion, which connects the liquid-aeriform separation chamber to a bottom portion of said heat-exchange evaporation chamber, wherein said connecting portion comprises a column that extends along a vertical axis, and
        iv) a recirculation pump for the tartaric acid solution, operatively connected to said connecting portion for recirculating the tartaric acid solution from said liquid-aeriform separation chamber to said heat-exchange evaporation chamber;
    wherein said first and second evaporation units are connected by a first pipe for transferring a partially concentrated tartaric acid solution, placed at a bottom portion of said evaporation units, and by a second pipe for transferring a properly aeriform phase from a head portion of said liquid-aeriform separation chamber of said first evaporation unit to said heat-exchange evaporation chamber of said second evaporation unit;
    wherein said liquid-aeriform separation chamber of said second evaporation unit is connected to said barometric condenser, an acidic solution separation chamber being placed in an intermediate position between said separation chamber of said second evaporation unit and said barometric condenser; and
    wherein said column of said connecting portion of said second evaporation unit comprises a pair of facing-flange pressure sensors, each coupled to a tantalum fluid separator, wherein said pressure sensors are placed at a distance of 2 m from each other pressure sensor and are connected to a differential pressure transmitter, wherein the pressure transmitter is connected in turn to a volumetric pump for extracting concentrated tartaric acid from the plant, said differential pressure transmitter being further connected to a flow rate sensor placed downstream of said volumetric pump, said volumetric pump being controlled on the basis of an electrical signal sent by said differential pressure transmitter between 4 mA and 20 mA, as measured by the pressure transmitter, and on the basis of a feedback control, sent by said flow rate sensor, the feedback control is adapted to keep the flow rate of concentrated tartaric acid flow exiting the plant within values between 0 m$^3$/h and 10 m$^3$/h.

2. The plant according to claim 1, wherein the first low-temperature vapor is saturated aqueous vapor having a temperature of 80° C.

3. The plant according to claim 1, wherein, inside said heat-exchange evaporation chamber of said second evaporation unit, the tartaric acid solution has a temperature of 56° C. and a pressure of 0.09 BarA; and wherein, inside said heat-exchange evaporation chamber of said first evaporation unit, the tartaric acid solution has a temperature of 66° C.

4. The plant according to claim 1, wherein said barometric condenser is connected to a vacuum pump and to a system for circulating water inside said barometric condenser, said barometric condenser condensing the properly aeriform phase exiting said second evaporation unit.

* * * * *